United States Patent [19]

Guigan

[11] 4,154,793
[45] May 15, 1979

[54] DEVICE FOR CONDITIONING A SAMPLE OF LIQUID FOR ANALYZING

[76] Inventor: Jean Guigan, 9, rue Jean Mermoz, 75008 Paris, France

[21] Appl. No.: 837,055

[22] Filed: Sep. 28, 1977

[30] Foreign Application Priority Data

Aug. 18, 1977 [FR] France .............................. 77 25225

[51] Int. Cl.² ..................... G01N 21/02; G01N 31/00; B04B 5/00; C12K 1/10
[52] U.S. Cl. ........................................ 422/55; 141/34; 195/127; 195/139; 233/27; 356/246; 356/427; 422/57; 422/72
[58] Field of Search ............... 23/253 R, 259; 141/34; 356/246; 233/27, 1 (U.S. only)

[56] References Cited

U.S. PATENT DOCUMENTS

| | | | |
|---|---|---|---|
| 3,415,361 | 12/1968 | Adams, Jr. et al. | 23/253 R X |
| 3,683,973 | 8/1972 | Hatcher, Sr. | 141/34 X |
| 3,770,027 | 11/1973 | Guigan | 23/259 X |
| 3,795,451 | 3/1974 | Mailen | 23/259 X |
| 3,876,377 | 4/1975 | Cinqualbre | 23/259 X |
| 3,890,101 | 6/1975 | Tiffany et al. | 23/259 |
| 3,986,534 | 10/1976 | Schmidt | 23/253 R X |
| 4,070,248 | 1/1978 | Schmidt | 195/139 X |

*Primary Examiner*—Joseph Scovronek
*Attorney, Agent, or Firm*—Sughrue, Rothwell, Mion, Zinn and Macpeak

[57] ABSTRACT

The invention relates to the conditioning of a sample of a liquid for medical analysis. The conditioning device according to the invention, comprises a plurality of calibrated peripheral cells connected to a central receptacle and includes, for each cell, ducts including an air inlet orifice for conveying the sample from the receptacle to said cell to completely fill the cell by centrifuging and an air escape orifice in each cell for the escape of the air contained in said cell closer to the axis of rotation than said inlet orifice and leading into said receptacle, said orifices further being dimensioned so as to retain the liquid contained in each cell after complete filling thereof.

12 Claims, 4 Drawing Figures

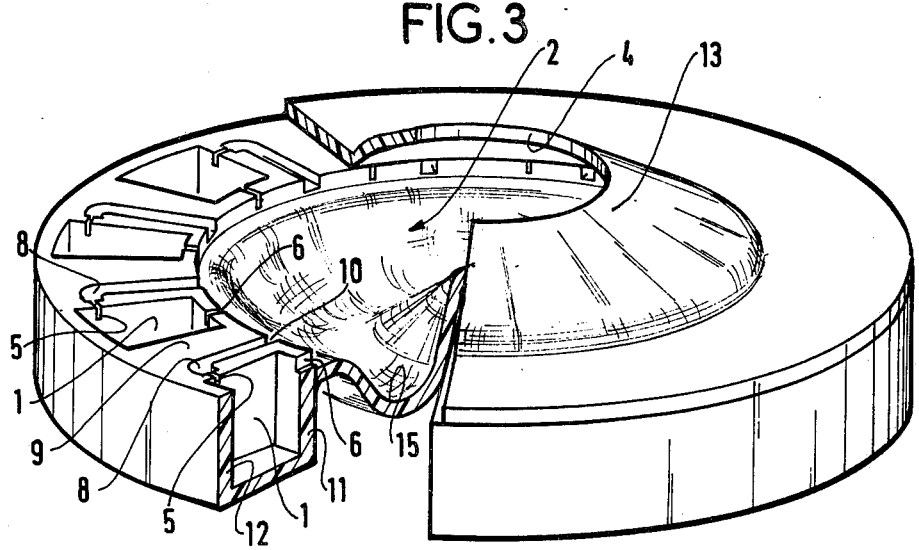
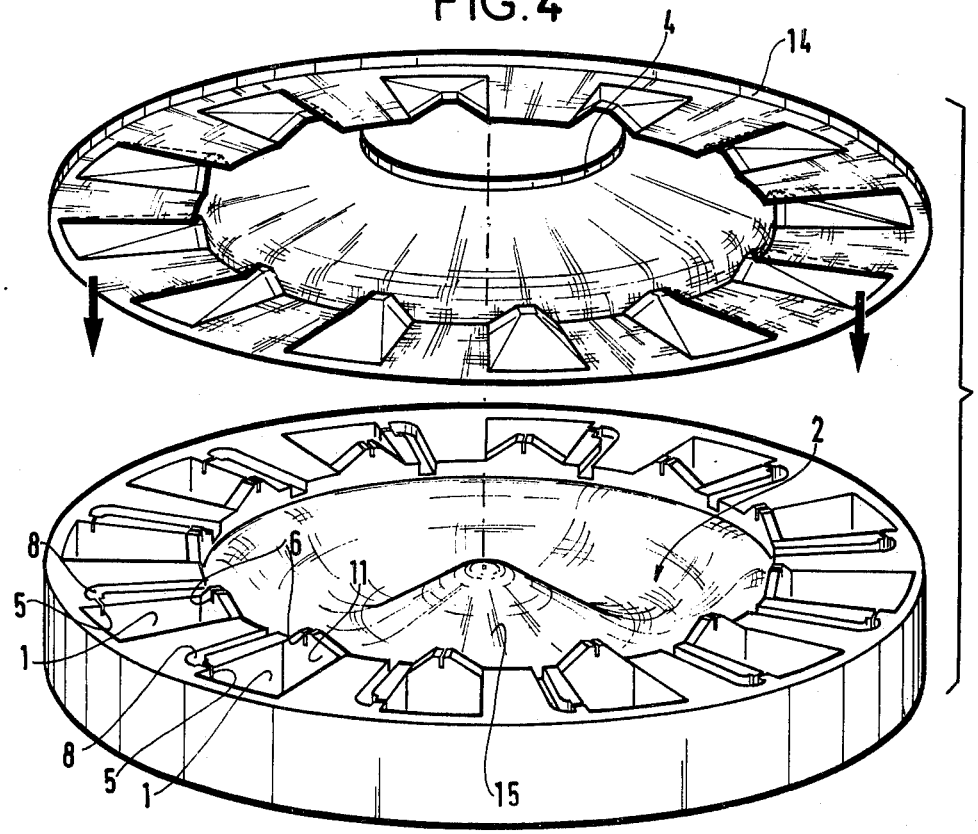

DEVICE FOR CONDITIONING A SAMPLE OF LIQUID FOR ANALYZING

FIELD OF THE INVENTION

The invention relates to the conditioning of a sample of liquid for analysis. The conditioning takes place in a rotary device which comprises a plurality of calibrated peripheral cells each having two parallel surfaces for optical measurement of the liquid and connected to a central receptacle for receiving said sample, each of said cells being intended to contain a reagent.

BACKGROUND OF THE INVENTION

It has already been proposed in the field of bacteriology to provide such devices constituted by a circular housing in which a central cup is provided for receiving the sample of bacterial suspension and from which there leaves a plurality of radial channels forming calibrated pipettes, each of said channels leading, by way of a capillary constriction, into an optical cup containing a culture medium and an antibiotic which are lyophilized (freeze dried). Thus the central cup and the channels are filled statically (the volume in each channel being calibrated by means of an end constriction). A stopper then simultaneously isolates all the radial channels, then rapid spinning transfers the liquid from each channel towards its associated optical cup (the centrifuging enabling the liquid to pass through the constrictions). These devices, although very efficient, nevertheless have some limits if it is required to use them for conventional analysis of a sample of liquid and not for bacteriology: indeed, the smaller dimensions remain limited by the presence of the calibrated pipettes which are already very small and end in a constriction. Now on site analysis by means of a portable analysis device requires further miniaturisation, with a conditioning device whose housing could, for example, have a diameter of the order of 4 centimeters, such miniaturisation is difficult to produce and excessively expensive when calibrated radial pipettes are used.

The present invention aims to provide a conditioning device whose design permits the use of very much smaller dimensions than those of previous devices, while remaining simple and suitable for mass-production by conventional moulding means.

The present invention provides a device for conditioning a sample of liquid with a view to analysing it. The device comprises a plurality of calibrated peripheral cells having two parallel surfaces for an optical measurement and connected to a central receptacle receiving said sample. Each of said cells is intended to contain a reagent. The device further comprises for each cell, means for conveying the sample from the receptacle to said cell with a view to filling it completely by centrifuging and escape means for air contained in said cell to said receptacle. The conveying means comprises an inlet orifice in each cell, and the escape means comprises an orifice nearer to the axis of rotation than said inlet orifice and leading into said receptacle. Each orifice is of such a size as to retain the liquid contained in each cell after complete filling thereof.

SUMMARY OF THE INVENTION

The device according to the invention preferably has at least one of the following characteristics:

The means for conveying the sample are constituted for each cell by at least one duct provided in a radial partition delimiting the cell, said duct connecting the central receptacle to the inlet orifice in the vicinity of which it has a constriction preventing any return of liquid, said inlet orifice leading from the radial partition preferably into the vicinity of the surface of the furthest cell from the axis of rotation.

The duct is substantially L-shaped and has a long radial path.

The duct is substantially T-shaped so as to feed two neighbouring cells and has a long radial path.

The duct is delimited by a groove formed in the upper surface of the associated radial partition and by a lower surface of a lid which closes the cells.

The duct is delimited by the upper surface of the associated radial partition and a groove formed in the lower surface of a lid blocking the cells.

Air escape means are constituted for each cell by a simple orifice formed in the surface of the nearest cell to the axis of rotation and whose cross-section allows, when there is no centrifuging, the stopping by capillarity of the liquid occupying said cell, said orifice being advantageously formed in the upper zone of said surface.

For each cell, the height of the nearest surface to the axis of rotation is greater than the height of the furthest surface from said axis, with a view to a better expulsion of the air contained in said cell.

The central receptacle is delimited by a bottom with a raised peripheral edge and the central part of a lid for closing the cells in which is formed an opening for the sample to be inserted, the central part of said lid preferably being substantially dome shaped, said insertion being formed at the top of said dome.

The bottom of the receptacle has a central zone which is curved with a view to improved centrifuging of the sample.

The bottom of the receptacle has a few radial ribs promoting the drawing away of the liquid during centrifuging.

The invention also relates to a device for analysing a sample of liquid, the device comprising a conditioning device such as previously defined associated with optical reading means and with means for displaying the results of the reading.

Other characteristics and advantages of the invention will become more clearly apparent from the following description, given by way of illustration but having no limiting character with reference to the figures of the accompanying drawings.

BRIEF DESCRIPTION OF THE DRAWINGS

FIG. 3 is a perspective view, partially cut away, of the device of FIG. 1;

FIG. 4 is a perspective view of a variant of the conditioning device embodying the invention, for an observer situated in an intermediate plane between the housing and the lid before they are assembled.

DESCRIPTION OF THE PREFERRED EMBODIMENTS

Figure 1:
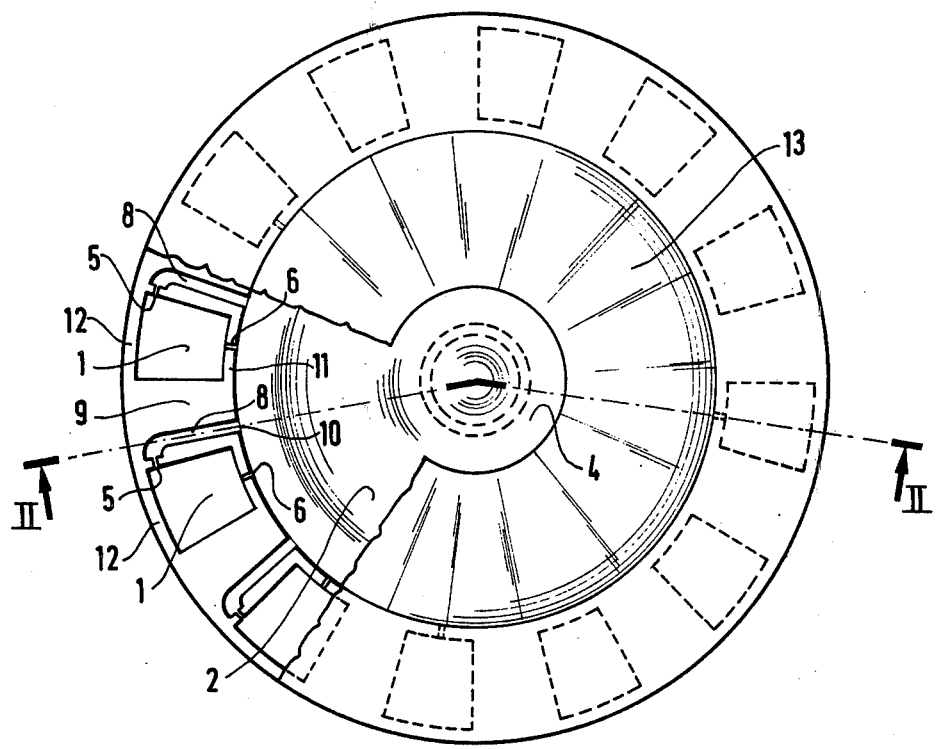
FIG. 1 is a top view of a conditioning device embodying the invention and whose lid has been partially cut away.
Figure 2:
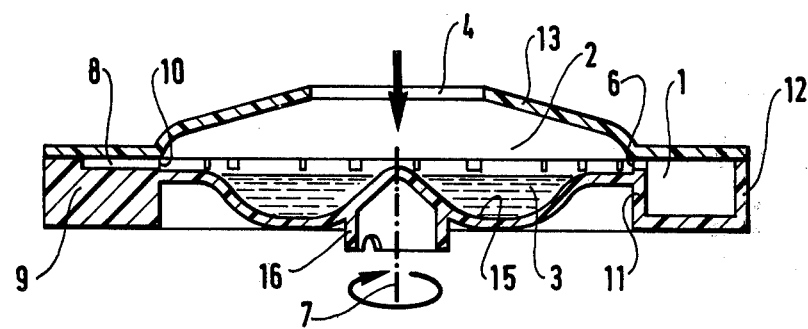
FIG. 2 is a cross-section along II—II of FIG. 1.

In FIGS. 1 to 3, a conditioning device comprises a plurality of calibrated peripheral cells 1 connected to a central receptacle 2. The cells each contain a reagent (not shown) deposited for example in the form of a lyophilized film and the receptacle receives the sample of liquid 3 (FIG. 2) with a view to analysing it, said sample being inserted through a central opening 4.

According to the fundamental principle of the invention, the cells are completely filled with the sample by centrifuging, the filling requiring an escape of the air contained in said cells, the constitution of the device making it possible to retain the liquid in the cells after centrifuging has ceased, so that the cell which acts as a reading chamber also fulfills a pipette function by virtue of its calibrated volume.

The means which will be described hereinafter allow complete filling of the cells and a complete escape of the air contained therein, while ensuring the maintenance of the volume of liquid of each cell and the independence of the liquid contents of one cell from another.

Thus, the device comprises for each cell firstly means for conveying the sample from the receptacle towards said cell and means for the air contained in said cell to escape towards said receptacle: fundamentally, said conveying means comprise an inlet orifice 5 in each cell and said escape means comprise an orifice 6, nearer to the axis of rotation 7 than said inlet orifice and leading into a receptacle 2, said orifices 5 and 6 being also dimensioned so as to retain the liquid contained in each cell after complete filling of the latter (the expression orifice being here taken in a wide sense, including for example a hole formed in a wall).

In the embodiment shown, the conveying means are constituted for each cell by at least one duct 8 formed in a radial partition 9 delimiting the cell, said duct connecting to central receptacle 2 by an input orifice 10 to the cell through the inlet orifice 5 in the vicinity of which it has a constriction preventing any return of liquid; the air escape means are constituted by a simple air escape orifice 6 formed in the nearest wall 11 of the cell to the axis of rotation and whose cross-section allows, when there is no centrifuging, the stopping by capillarity of the liquid occupying said cell.

Thus, when rapid centrifuging is imparted to the sample of liquid, this sample is pushed strongly against the orifices 6 and 10: the portion passing through the orifice 10 is canalized by the duct 8 up to the capillary end of the latter and to the inlet orifice 5. The input pressure at 5 is constantly greater than the input pressure at 6 because of the centrifugal force and of its being further from the axis of rotation, so that the air contained in the cell is pushed by the liquid and escapes at 6; the filling continues until the air has completely escaped and balances the pressure on either side of the wall 11, as there is provided a sufficient quantity of sample for a portion thereof to be applied against the wall 11, even when the cell is completely filled. During the whole filling and until the end of filling, any portion of liquid which has entered a cell cannot leave it because of the centrifugal force and when centrifuging ceases, the liquid completely occupying the cell is retained between the orifices 5, 6 which thus form genuine gauge points defining a calibrated volume.

Inasmuch as concerns the means of conveying the sample, the orifice 5 advantageously leads to the vicinity of the wall 12 of the cell wall further from the axis of rotation 7, so as to take the best advantage of the centrifuging effect.

The duct 8 is substantially L shaped and has a long radial path. A T shaped duct could also be provided so as to feed two neighboring cells. For easy manufacturing of the device, the duct 8 is delimited by a groove formed on the upper surface of the associated radial partition 9 and by the lower surface of a lid 13 closing the cells; conversely, it would also be possible to provide a duct delimited by the plane upper surface of the radial partition and a groove formed on the lower surface of a lid closing the cells.

It is advantageous for good escape of the air for the orifice 6 to be formed in the upper zone of the wall 11. This principle is shown even better in a variant of the device according to the invention illustrated in FIG. 4, for which variant the height of the wall 11 is, for each cell, greater than that of the wall 12 for a better expulsion of the air. In this variant, the cover 14 (here seen from below) has a shape adapted to closing the cells whose wall 11 is extended upwards and for application against the radial partitions for the delimitation of the conveying ducts. The orifice 6 is here delimited by a simple capillary groove formed at the top of the walls 11 and by the adjacent portion of the lower wall of the lid 14. By way of indication, this capillary groove, just like the downstream end of the duct leading into each cell through the orifice 5, can be or the order of a few hundredths of a millimeter in diameter.

For the two variants described, the central receptacle 2 is delimited by a bottom 15 with a raised peripheral edge and whose central zone is advantageously curved with a view to a better centrifuging of the sample and by the central part of a lid (13 or 14 according to the variant), advantageously dome shaped or conical for a better application of the sample against the wall 11 during centrifuging. A few radial ribs (not shown) can also be provided on the bottom of the receptacle to promote the drawing off of the liquid during centrifuging.

In a way known per se, the bottom 15 has protruding drawing off means 16. It should be observed that these means and the opening 4 of the lids are advantageously dimensioned for stacking with minimum bulk of several conditioning devices.

The housing and the lid, formed by high-pressure moulding, are assembled by high-frequency welding or any other equivalent means.

The invention also relates to a device for analysis of a sample of liquid comprising a conditioning device such as previously described according to any one of the possible variants, associated with optical reading means and with means for displaying the results of the reading.

It is self-evident that the present invention is in no way limited to the examples which have been given thereof by way of illustration, but comprises any variant having equivalent means to those of the general definition of the invention as claimed.

What is claimed is:

1. A device for conditioning a sample of liquid for analyzation, said device comprising:
   a central receptacle,
   a plurality of calibrated peripheral cells on the periphery of the central receptacle, each cell having two parallel walls for an optical measurement and connected to said central receptacle receiving said sample, each of said cells being a reagent receiving cell said device further comprising for each cell, means for conveying the sample of liquid from the receptacle to said cell to fill it completely by centrifuging and escape means for the air contained in said cell to said receptacle, said conveying means comprising an inlet orifice in each cell, said escape means comprising an orifice nearer to the axis of rotation than said inlet orifice and leading into said receptacle, and said orifices being of such a size as to retain the liquid contained in each cell after complete filling thereof and centrifuging has ceased.

2. A device according to claim 1, wherein each cell is delimited by a radial partition, the means for conveying the sample comprise for each cell at least one duct formed in said radial partition, said duct connecting the central receptacle to the inlet orifice and a constriction within said duct in the vicinity of said inlet orifice for preventing any return of liquid.

3. A device according to claim 2, wherein said at least one duct leads from the radially inner end of said radial partition to the neighborhood of the cell wall farther from the axis of rotation.

4. A device according to claim 2, wherein said at least one duct is substantially L shaped and has a long radial path.

5. A device according to claim 2, wherein said cells are closed off by a lid and said at least one duct is delimited by a groove formed on the upper surface of the associated radial partition and by the lower surface of said lid closing the cells.

6. A device according to claim 2, wherein said cells are closed off by a lid and said at least one duct is delimited by the upper surface of the associated radial partition and a groove formed on the lower surface of a lid closing the cells.

7. A device according to claim 1, wherein the cells are partially defined by vertical walls and the air escape means comprise for each cell, a simple air escape orifice formed in the cell wall nearer to the axis of rotation and whose cross-section is such that when there is no centrifuging the stopping of flow of liquid by capillarity of the liquid occupying said cell within said air escape orifice occurs.

8. A device according to claim 7, wherein the air escape orifice is formed in the upper zone of said wall.

9. A device according to claim 7, wherein for each cell, the height of the cell wall nearer to the axis of rotation is greater than the height of the cell wall farther from said axis, to provide better expulsion of the air contained in said cell.

10. A device according to claim 1, wherein the cells are closed off by a lid and the central receptacle is delimited by a bottom with a raised peripheral edge and the central part of said lid for closing the cells in which is formed an opening for the insertion of the sample.

11. A device according to claim 10, wherein the central part of the lid is substantially dome shaped and said insertion hole being formed in the top of said dome.

12. A device according to claim 10, wherein the bottom of the receptacle has a curved central zone to improve the centrifuging of the sample.

* * * * *